United States Patent
Kitahara et al.

(10) Patent No.: US 11,377,631 B2
(45) Date of Patent: Jul. 5, 2022

(54) CULTURE CONTAINER LINKAGE DEVICE, CULTURE SYSTEM, AND METHOD FOR WASHING NEEDLE

(71) Applicant: Sinfonia Technology Co., Ltd., Tokyo (JP)

(72) Inventors: Toshifumi Kitahara, Tokyo (JP); Kunitada Hatabayashi, Tokyo (JP); Kiyoshi Mori, Tokyo (JP); Hirotsugu Shiraiwa, Tokyo (JP)

(73) Assignee: Sinfonia Technology Co., Ltd., Tokyo (JP)

( * ) Notice: Subject to any disclaimer, the term of this patent is extended or adjusted under 35 U.S.C. 154(b) by 708 days.

(21) Appl. No.: 16/341,493

(22) PCT Filed: Oct. 11, 2017

(86) PCT No.: PCT/JP2017/036881
§ 371 (c)(1),
(2) Date: Apr. 12, 2019

(87) PCT Pub. No.: WO2018/070447
PCT Pub. Date: Apr. 19, 2018

(65) Prior Publication Data
US 2019/0241860 A1    Aug. 8, 2019

(30) Foreign Application Priority Data
Oct. 13, 2016   (JP) ............................... JP2016-201996

(51) Int. Cl.
*C12M 1/12*    (2006.01)
*C12M 1/00*    (2006.01)
(Continued)

(52) U.S. Cl.
CPC ............... *C12M 37/00* (2013.01); *A61L 2/04* (2013.01); *B08B 9/00* (2013.01); *C12M 1/00* (2013.01);
(Continued)

(58) Field of Classification Search
CPC ........ C12M 37/00; C12M 1/00; C12M 23/46; C12M 23/50; C12M 27/00; C12M 29/18;
(Continued)

(56) References Cited

U.S. PATENT DOCUMENTS

2006/0257999 A1   11/2006   Chang et al.
2010/0248343 A1*   9/2010   Aten ...................... C12M 35/02
435/283.1
(Continued)

FOREIGN PATENT DOCUMENTS

EP    3109312    12/2016
JP    61-274675  12/1986
(Continued)

OTHER PUBLICATIONS

Europe Patent Application No. 17860820.4, Extended European Search Report, dated May 6, 2020, 8 pages.
(Continued)

*Primary Examiner* — Michael L Hobbs
(74) *Attorney, Agent, or Firm* — Kilpatrick Townsend & Stockton LLP

(57) ABSTRACT

A culture container linkage device according to the present disclosure includes a first actuator configured to advance or retract needles 32, an actuator holder rotatably provided on a frame and configured to hold the first actuator, a second actuator, and a washer configured to wash the needles. The second actuator rotates the needles via the actuator holder. The needles are configured to be positioned, by the second actuator, at a container-facing position at which the needles
(Continued)

face a culture container and a washing-facing position at which the needles face the washer.

15 Claims, 11 Drawing Sheets

(51) Int. Cl.
    *A61L 2/04*     (2006.01)
    *C12M 3/00*     (2006.01)
    *C12M 1/02*     (2006.01)
    *B08B 9/00*     (2006.01)

(52) U.S. Cl.
    CPC .............. *C12M 3/00* (2013.01); *C12M 23/46* (2013.01); *C12M 23/50* (2013.01); *C12M 27/00* (2013.01); *C12M 29/18* (2013.01); *C12M 39/00* (2013.01)

(58) Field of Classification Search
    CPC ...... C12M 33/00; C12M 39/00; C12M 41/48; A61L 2/04; B08B 9/00
    See application file for complete search history.

(56) References Cited

U.S. PATENT DOCUMENTS

| | | |
|---|---|---|
| 2015/0369834 A1 | 12/2015 | Tokumaru |
| 2018/0044624 A1 | 2/2018 | Shiraiwa |

FOREIGN PATENT DOCUMENTS

| | | |
|---|---|---|
| JP | 2004-512514 | 4/2004 |
| JP | 2015-109877 | 6/2015 |
| WO | 2002034944 | 5/2002 |
| WO | 2015125742 | 8/2015 |
| WO | 2016133209 A1 | 8/2016 |

OTHER PUBLICATIONS

International Patent Application No. PCT/JP2017/036881, International Search Report, dated Jan. 9, 2018.

* cited by examiner

CULTURE CONTAINER LINKAGE DEVICE, CULTURE SYSTEM, AND METHOD FOR WASHING NEEDLE

TECHNICAL FIELD

The present disclosure relates to a culture container linkage device, a culture system, and a method for washing a needle.

BACKGROUND

In recent years, there has been research and development of regenerative medicine in which a target tissue or organ is artificially created by cell culture. In order to carry out a cell culture operation or the like, a culture system which satisfies predetermined criteria, for example, a GMP (Good Manufacturing Practice) is used.

In a culture system, usually, a liquid culture medium (also referred to as culture solution) contained in a culture container is periodically replaced in order to prevent a culture environment in the culture container from being gradually deteriorated. At this time, by supplying a new culture medium to the culture container, an old culture medium contained in the culture container is pushed out and discharged from the culture container (see, e.g., Patent Document 1).

PRIOR ART DOCUMENTS

Patent Documents

Patent Document 1: Japanese laid-open publication No. 2015-109877

When using a closed-type culture container, two needles are inserted into the culture container through a rubber plug which closes an inlet of the culture container and a rubber plug which closes an outlet of the culture container, and the culture medium is replaced. At the time of replacing the culture medium, a new culture medium is supplied to the culture container via one of the needles, and an old culture medium is discharged from the culture container via the other needle. It is usual to use disposable needles in order to prevent contamination of the culture medium.

However, when using disposable needles, the needles are replaced after replacing the culture medium. For this reason, there is a problem that it takes time and effort for the culture medium replacement operation.

The present disclosure has been made in consideration of such a problem, and provides a culture container linkage device, a culture system, and a method for washing a needle, which are capable of improving the efficiency of a culture medium replacement operation.

SUMMARY

According to one embodiment of the present disclosure, there is provided a culture container linkage device, to which a culture container is linked when a culture medium is replaced, including: a frame; a container holder provided on the frame and configured to hold the culture container; two needles held by a needle holder and configured to be advanced into or retreated from the culture container held by the container holder, the culture medium in the culture container being replaced by the needles; a first actuator configured to advance or retract the needles; an actuator holder rotatably provided on the frame and configured to hold the first actuator; a second actuator configured to rotate the needles via the actuator holder; and a washer provided such that the needles are advanced into or retreated from the washer, and configured to wash the needles, wherein the container holder and the washer are disposed at different positions in a rotation direction of the needles, and the needles are configured to be positioned, by the second actuator, at a container-facing position at which the needles face the culture container held by the container holder and a washing-facing position at which the needles face the washer.

The device described above may further include an engager configured to engage with the actuator holder, wherein the second actuator may be configured to move the engager forward and backward while holding the engager, and the actuator holder may include a converter engaged with the engager and configured to convert a forward-backward movement of the engager into a rotational movement of the needles.

In the device described above, the second actuator may be held by the actuator holder, and the second actuator may include a rotation shaft non-rotatably fixed to the frame, the second actuator configured to rotate the needles via the actuator holder by rotating the actuator holder with a reaction force against the frame.

In the device described above, the washer may include: an internal washing hole provided such that the needles are advanced into or retracted from the internal washing hole, and configured to perform internal washing of the needles; and an external washing hole provided such that the needles are advanced into or retracted from the external washing hole, and configured to perform external washing of the needles, the internal washing hole and the external washing hole may be disposed at different positions in the rotation direction of the needles, the washing-facing position may include an internal washing-facing position at which the needles face the internal washing hole and an external washing-facing position at which the needles face the external washing hole, and the needles may be configured to be positioned at the internal washing-facing position and the external washing-facing position by the second actuator.

The device described above may further include a bypass part provided such that the needles are advanced into or retracted from the bypass part, and configured to bring the needles into communication with each other, wherein the bypass part may be disposed at a position different from the positions of the container holder and the washer in the rotation direction of the needles, and the needles may be configured to be positioned, by the second actuator, at a bypass-facing position at which the needles face the bypass part.

The device described above may further include a sterilizer provided such that the needles are advanced into or retracted from the sterilizer, and configured to sterilize the needles, wherein the sterilizer may be disposed at a position different from the positions of the container holder and the washer in the rotation direction of the needles, and the needles may be configured to be positioned, by the second actuator, at a sterilization-facing position at which the needles face the sterilizer.

According to another embodiment of the present disclosure, there is provided a culture system including: the culture container linkage device described above; a buffer tank configured to store a new culture medium; and a culture medium discharge driver configured to discharges the culture medium from the culture container held by the container holder of the culture container linkage device, wherein one of the needles of the culture container linkage device is connected to the buffer tank, and the other of the needles is connected to the culture medium discharge driver.

According to a further embodiment of the present disclosure, there is provided a method for washing two needles of a culture container linkage device to be linked to a culture container when a culture medium is replaced, including: inserting the needles into the culture container and replacing the culture medium in the culture container; positioning the needles at a container-facing position at which the needles face the culture container, by retracting the needles from the culture container; and positioning the needles at a washing-facing position at which the needles face a washer for washing the needles, by rotating the needles from the container-facing position, advancing the needles from the washing-facing position, and washing the needles in the washer.

In the method described above, the culture container linkage device may include a first actuator, an actuator holder configured to hold the first actuator, and a second actuator configured to rotate the actuator holder, the needles may be advanced and retracted by the first actuator, and the needles may be rotated by the second actuator.

In the method described above, the culture container linkage device may further include an engager configured to engage with the actuator holder, the second actuator may be configured to move the engager forward and backward while holding the engager, and the actuator holder may include a converter engaged with the engager and configured to convert a forward-backward movement of the engager into a rotational movement of the needles.

In the method described above, the culture container linkage device may further include a frame on which the actuator holder is rotatably provided, the second actuator may be held by the actuator holder, and the second actuator may include a rotation shaft non-rotatably fixed to the frame, the second actuator configured to rotate the needles via the actuator holder by rotating the actuator holder with a reaction force against the frame.

In the method described above, the washer may include an internal washing hole configured to perform internal washing of the needles, and an external washing hole configured to perform external washing of the needles, the washing-facing position may include an internal washing-facing position at which the needles face the internal washing hole and an external washing-facing position at which the needles face the external washing hole, and the act of washing the needles may include: positioning the needles at the internal washing-facing position; advancing the needles from the internal washing-facing position and internally washing the needles in the internal washing hole; positioning the needles at the internal washing-facing position by retracting the needles from the internal washing hole; positioning the needles at the external washing-facing position by rotating the needles from the internal washing-facing position; and advancing the needles from the external washing-facing position and externally washing the needles in the external washing hole.

The method described above may further include: positioning the needles at the washing-facing position by retracting the needles from the washer; positioning the needles at a bypass-facing position at which the needles face a bypass part for bringing the needles into communication with each other, by rotating the needles from the washing-facing position; and advancing the needles from the bypass-facing position and bringing the needles into communication with each other in the bypass part.

The method described above may further include: positioning the needles at the washing-facing position by retracting the needles from the washer; positioning the needles at a sterilization-facing position at which the needles face a sterilizer for sterilizing the needles, by rotating the needles from the washing-facing position; and advancing the needles from the sterilization-facing position and sterilizing the needles in the sterilizer.

The method described above may further include: positioning the needles at the sterilization-facing position by retracting the needles from the sterilizer; positioning the needles at a bypass-facing position at which the needles face a bypass part for bringing the needles into communication with each other, by rotating the needles from the sterilization-facing position; and advancing the needles from the bypass-facing position and bringing the needles into communication with each other in the bypass part.

According to the present disclosure, it is possible to improve the efficiency of a culture medium replacement operation.

DETAILED DESCRIPTION

Figure 1:
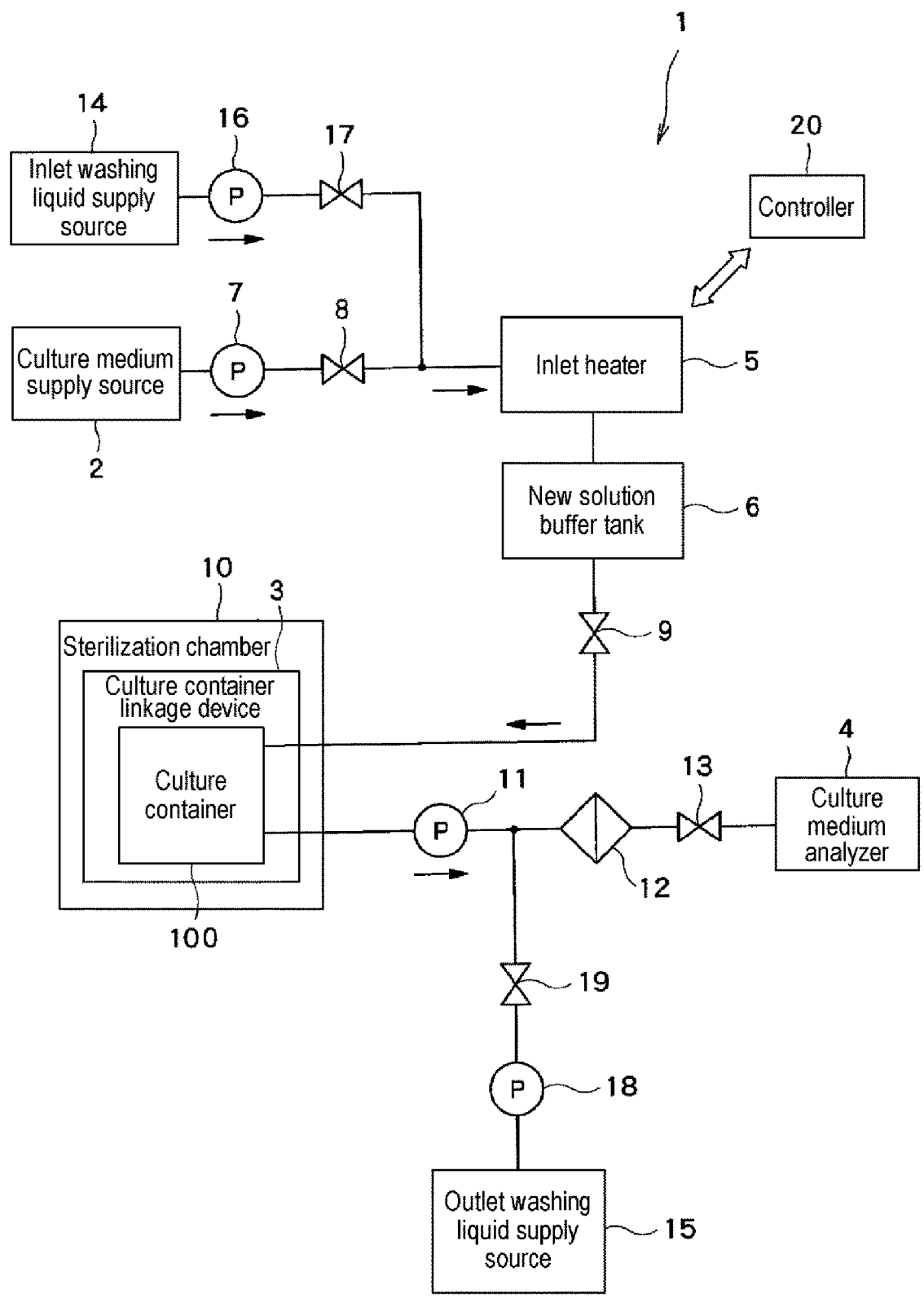
FIG. 1 is a view showing a schematic configuration of a culture system according to a first embodiment.

Hereinafter, embodiments of the present disclosure will be described with reference to the drawings. In the drawings attached to this specification, for the sake of easy-to-understand illustration, the scale, the vertical and horizontal dimension ratio, and the like are appropriately changed and exaggerated from those of the real thing.

The culture system according to each embodiment may be used to culture any cell, and may be used when culturing various cells including pluripotent stem cells such as (Human) iPS cells, (human) ES cells and the like, chondrocytes such as bone marrow stromal cells (MSC) and the like, dendritic cells, and so forth. In each embodiment, the following description will be mainly made on the assumption that iPS cells are cultured. However, this is merely an example.

First Embodiment

First, the schematic configuration of a culture system according to a first embodiment of the present disclosure will be described with reference to FIG. 1.

As shown in FIG. 1, the culture system 1 includes a culture medium supply source 2 configured to supply a new culture medium, a culture container linkage device 3 to which a culture container 100 for culturing cells is linked at the time of culture medium replacement, and a culture medium analyzer 4 configured to analyze components of the culture medium discharged from the culture container 100 linked to the culture container linkage device 3.

The culture medium supply source 2 stores a new culture medium for cell culture to be supplied to the culture container 100. The culture medium supply source 2 is provided, for example, in a cold storage. At the time of storage, the culture medium is stored at a low temperature (for example, about 4 degrees C.) to prevent deterioration of components.

An inlet heater 5 and a new solution buffer tank 6 are provided in this order between the culture medium supply source 2 and the culture container linkage device 3.

The inlet heater 5 heats the culture medium supplied from the culture medium supply source 2 to the culture container 100 to increase the temperature of the culture medium to a high temperature (for example, about 37 degrees C.). The heated culture medium is discharged from the inlet heater 5 and supplied to the new solution buffer tank 6. An inlet pump 7 for supplying the culture medium from the culture medium supply source 2 to the new solution buffer tank 6 via the inlet heater 5 is provided between the culture medium supply source 2 and the inlet heater 5.

The new solution buffer tank 6 stores the culture medium heated by the inlet heater 5 and removes air bubbles in the culture medium. The new solution buffer tank 6 includes an internal space for storing a culture medium and a vent (both of which are not shown). The internal space in the new solution buffer tank 6 communicates with the surrounding atmosphere of the new solution buffer tank 6 (the clean atmosphere in a chamber in which the new solution buffer tank 6 is accommodated) via the vent. Thus, when air bubbles are mixed in the culture medium stored in the new solution buffer tank 6, the air bubbles float up and are removed from the culture medium. That is, the air bubbles contained in the new culture medium expand due to the high temperature, whereby the air bubbles can be efficiently removed from the culture medium stored in the internal space. Furthermore, by providing the vent, the supply and discharge of the culture medium to and from the new solution buffer tank 6 can be made smooth. A vent filter (not shown) is provided in the vent to prevent the entry of foreign substances into the internal space of the new solution buffer tank 6.

The storage capacity of the culture medium in the internal space of the new solution buffer tank 6 is preferably larger than the capacity of the culture container 100 such that it is possible to supply a culture medium for pushing out the old culture medium in the culture container 100 when the culture medium in the culture container 100 is replaced. For example, when the capacity of the culture container 100 is 18 mL, the culture medium storage capacity of the new solution buffer tank 6 may be, for example, 30 mL which is larger than the capacity of the culture container 100.

A first inlet opening/closing valve 8 is provided between the inlet pump 7 and the inlet heater 5. The first inlet opening/closing valve 8 controls the supply of the culture medium from the culture medium supply source 2 to the new solution buffer tank 6. A second inlet opening/closing valve 9 is provided between the new solution buffer tank 6 and the culture container linkage device 3 to control the supply of the culture medium from the new solution buffer tank 6 to the culture container 100. The new solution buffer tank 6 is disposed at a position higher than the culture container linkage device 3. Thus, it is possible to easily supply the culture medium from the new solution buffer tank 6 to the culture container 100 linked to the culture container linkage device 3.

The culture container linkage device 3 is configured to hold and link the culture container 100. The culture container linkage device 3 is accommodated in a sterilization chamber 10. The sterilization chamber 10 is configured to adjust at least one of the temperature, humidity and gas concentration of the linked culture container 100. For example, the sterilization chamber 10 adjusts the temperature of the atmosphere such that the temperature of the culture container 100 becomes about 37 degrees C. The inside of the sterilization chamber 10 is a sterilization space. Details of the culture container 100 will be described later.

An outlet pump 11 (a culture medium discharge driver), a culture medium filter 12 and an outlet opening/closing valve 13 are provided in this order between the culture container linkage device 3 and the culture medium analyzer 4. Among them, the outlet pump 11 withdraws the culture medium after cell culture from the culture container 100, discharges the culture medium, and supplies the culture medium to the culture medium analyzer 4. At this time, the supply of a new culture medium from the new solution buffer tank 6 to the culture container 100 is promoted simultaneously with the withdrawal of the culture medium from the culture container 100. As a result, the new culture medium is supplied to the culture container 100, whereby culture medium replacement is performed. The culture medium filter 12 is configured to remove solid materials (for example, cells under culture or the like) contained in the culture medium discharged from the culture container 100. The outlet opening/closing valve 13 is configured to control the supply of the culture medium from the culture container 100 to the culture medium analyzer 4.

The culture system 1 according to the present embodiment further includes an inlet washing liquid supply source 14 and an outlet washing liquid supply source 15. Among them, the inlet washing liquid supply source 14 supplies a washing liquid (for example, pure water) to a first needle 32a via the inlet heater 5 and the new solution buffer tank 6 in order to wash the first needle 32a (described later). An inlet washing pump 16 and an inlet washing opening/closing valve 17 are provided in this order between the inlet washing liquid supply source 14 and the inlet heater 5 to control the supply of a washing liquid from the inlet washing liquid supply source 14 to the first needle 32a. The outlet washing liquid supply source 15 supplies a washing liquid (for example, pure water) to a second needle 32b via the outlet pump 11 in order to wash the second needle 32b (described later). An outlet washing pump 18 and an outlet washing opening/closing valve 19 are provided in this order between the outlet washing liquid supply source 15 and the outlet pump 11 to control the supply of a washing liquid from the outlet washing liquid supply source 15 to the second needle 32b.

As shown in FIG. 1, the culture system 1 further includes a controller 20. The controller 20 is configured to control the above-described opening/closing valves and pumps.

Next, the culture container 100 according to the present embodiment will be described using FIGS. 2 and 3. The culture container 100 of a culture plate type will be described as an example.

Figure 2:
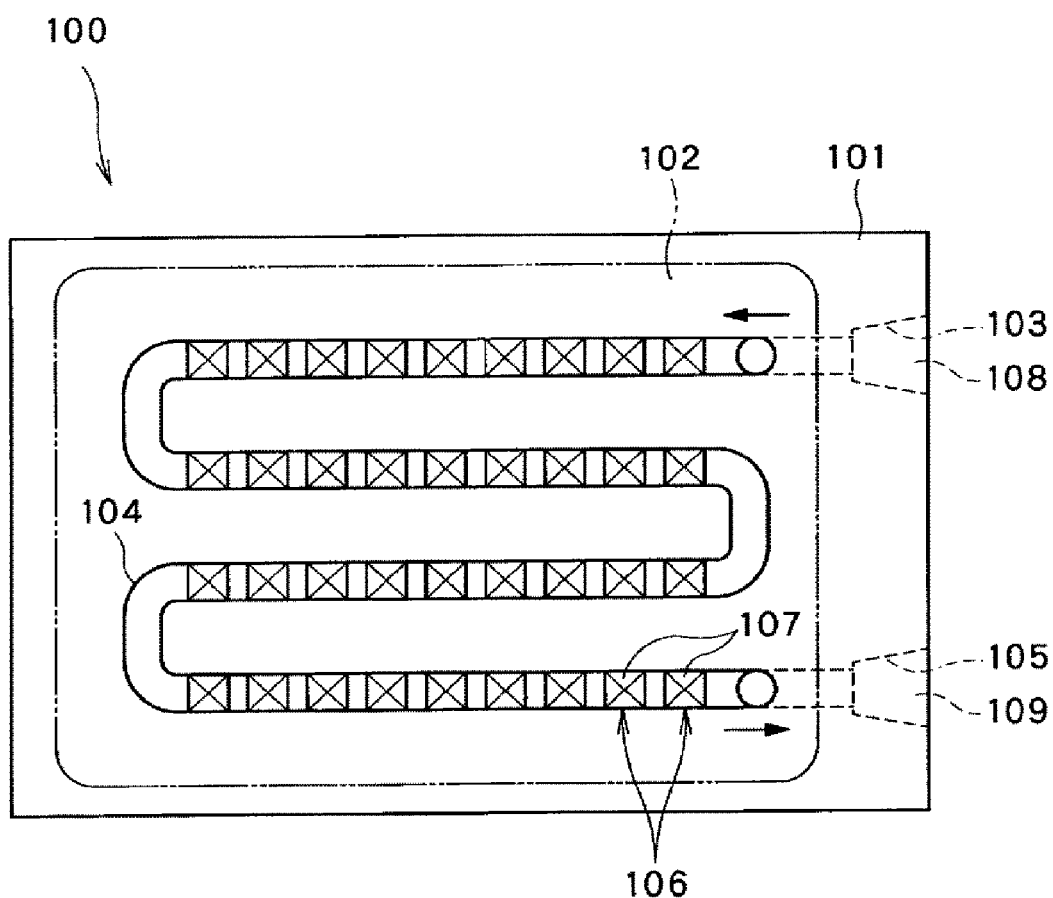
FIG. 2 is a plan view showing a culture container shown in FIG. 1.
Figure 3:
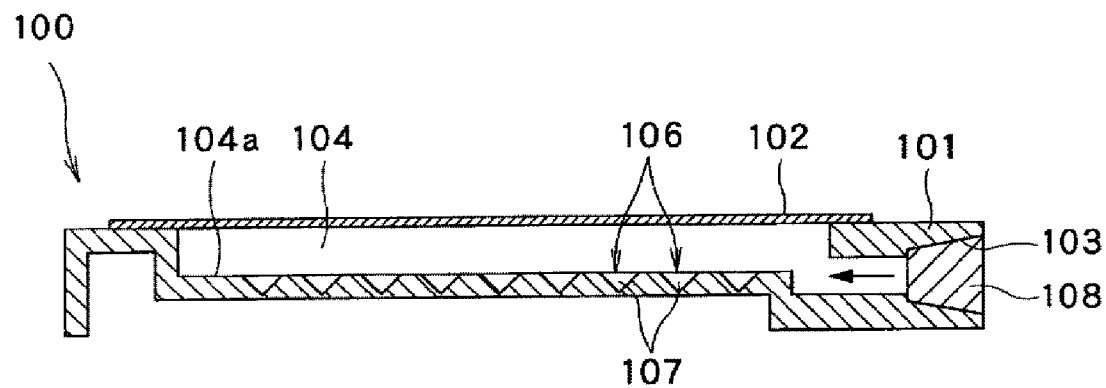
FIG. 3 is a sectional view showing the culture container shown in FIG. 2.

As shown in FIGS. 2 and 3, the culture container 100 includes a container body 101 and a flat plate 102 attached to one surface of the container body 101. The container body 101 includes an inlet 103 through which a culture medium (a suspension in which cells are dispersed, a release agent, a phosphate buffered saline (PBS), etc., in addition to the culture medium) flows inward, a passage 104 through which the culture medium flowing from the inlet 103 passes, and an outlet 105 through which the culture medium having passed through the passage 104 flows outward. Among them, the inlet 103 is connected to the new solution buffer tank 6 described above, and the outlet 105 is connected to the culture medium analyzer 4.

The passage 104 of the container body 101 is formed in a groove shape on one surface side of the container body 101 to which the flat plate 102 is attached. The diameter of the passage 104 (i.e., the depth and width of a groove) is, for example, 2 mm to 4 mm. Furthermore, the passage 104 of the container body 101 has a meandering portion in a plan view, i.e., a portion in which linear portions and folded portions are alternately connected. As a result, the total length of the passage 104 is extended without increasing the size of the container body 101, whereby an elongated passage 104 is formed.

As shown in FIGS. 2 and 3, on a passage bottom surface 104a of the passage 104, a plurality of cell seeding areas 106 in which cells passing through the passage 104 are seeded are provided side by side along the passage 104. In the present embodiment, a recess 107 is provided in the passage bottom surface 104a of the passage 104 concentrically with the cell seeding areas 106.

An inlet rubber plug 108 is inserted into the inlet 103, and an outlet rubber plug 109 is inserted into the outlet 105, whereby the inlet 103 and the outlet 105 are closed. Needles 32, which will be described later, may penetrate the inlet rubber plug 108 and the outlet rubber plug 109.

When the culture medium in the culture container 100 is replaced, the outlet pump 11 is driven in a state in which the needles described later are connected to the inlet rubber plug 108 and the outlet rubber plug 109, respectively, and the old culture medium in the passage 104 is withdrawn and drained from the outlet 105. Along with this, the new culture medium supplied from the new solution buffer tank 6 flows into the passage 104 from the inlet 103. During this time, the old culture medium in the passage 104 flows out from the outlet 105 as the old culture medium is pushed out by the new culture medium. In this case, the new culture medium and the old culture medium flow along the passage 104. It is therefore possible to prevent the new culture medium and the old culture medium from being mixed with each other and the easily replace the old culture medium with the new culture medium.

Next, the culture container linkage device 3 according to the first embodiment of the present disclosure will be described using FIGS. 4 to 6. The culture container linkage device 3 is provided in the sterilization chamber 10 described above.

Figure 4:
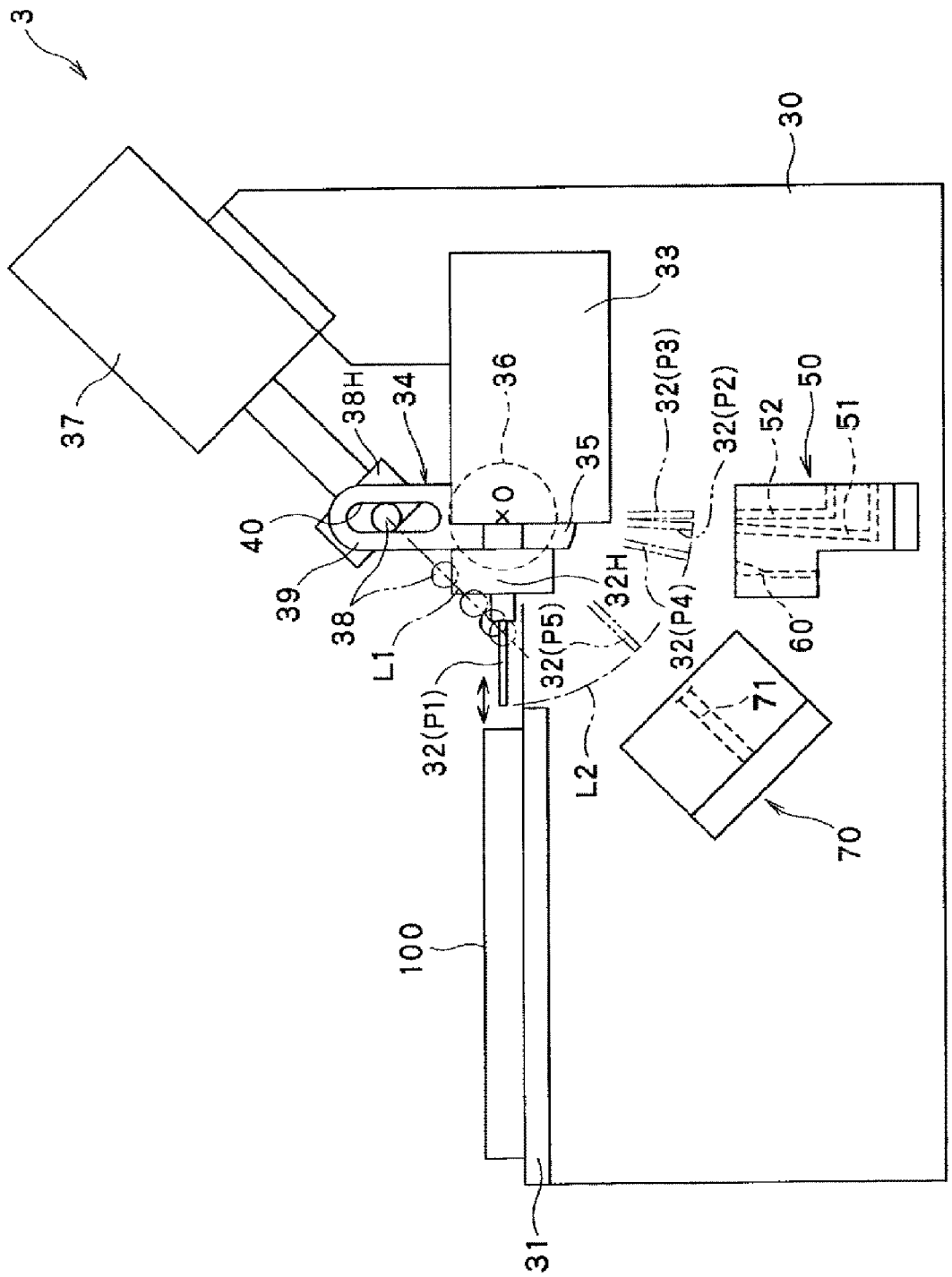
FIG. 4 is a schematic configuration view showing a culture container linkage device shown in FIG. 1.
Figure 5:
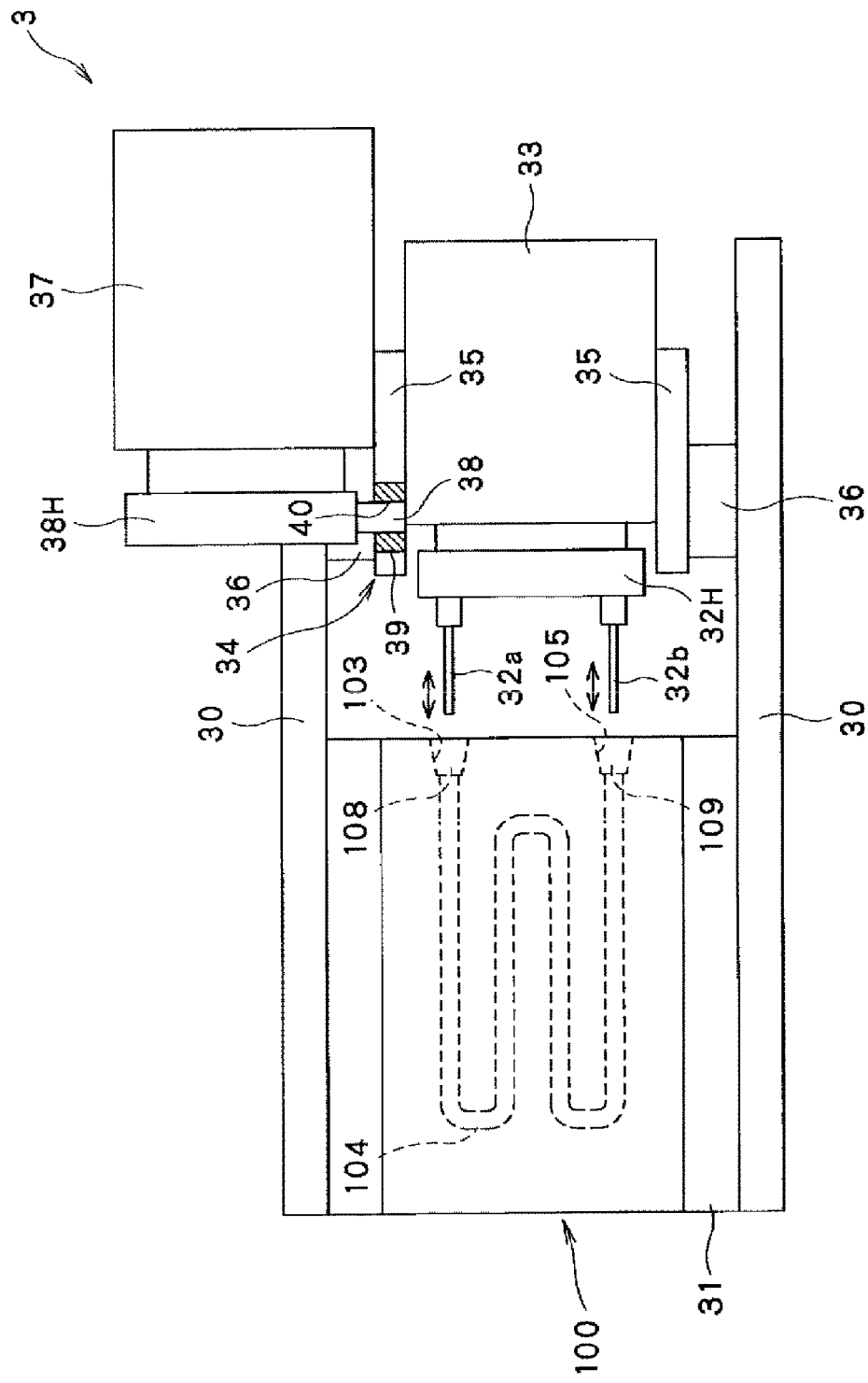
FIG. 5 is a schematic plan view showing the culture container linkage device shown in FIG. 4.

As shown in FIGS. 4 and 5, the culture container linkage device 3 includes a pair of frames 30, a container holder 31 provided in the pair of frames 30 to hold the culture container 100, two needles 32 configured to replace the culture medium in the culture container 100 held by the container holder 31, and a first actuator 33. Among them, the frames 30 are erected and provided parallel to each other, and are integrated by a connecting member (not shown). As shown in FIG. 5, the container holder 31 is arranged between the frames 30, and is supported by the respective frames 30.

The needles 32 are capable of advancing to and retreating from the culture container 100 held by the container holder 31. One of the two needles 32 (first needle 32a) is connected to the new solution buffer tank 6 described above, and the other (second needle 32b) is connected to the culture medium analyzer 4 described above. The two needles 32 are held by a needle holder 32H. The inlet 103 and the outlet 105 of the culture container 100 held by the container holder 31 are spaced apart and arranged side by side in the axial direction of a rotation shaft 36 of an actuator holder 34 (all of which will be described later). Similarly, the two needles 32 are arranged side by side in the axial direction of the rotation shaft 36 and disposed at the same interval as the inlet 103 and the outlet 105 of the culture container 100. Thus, the two needles 32 are inserted into the culture container 100 at the time of culture medium replacement. More specifically, the first needle 32a is inserted into the inlet 103 through the inlet rubber plug 108 fitted to the inlet 103 of the culture container 100, and a new culture medium is supplied from the new solution buffer tank 6 to the culture container 100 through the first needle 32a. On the other hand, the second needle 32b is inserted into the outlet 105 through the outlet rubber plug 109 fitted to the outlet 105, and the culture medium in the culture container 100 is discharged through the second needle 32b.

The first actuator 33 is disposed between the frames 30 to move the two needles 32 back and forth (forward and backward). More specifically, the first actuator 33 holds the needle holder 32H and linearly moves the needle holder 32H along the longitudinal direction of the needles 32 (the left-right direction in FIG. 4) to linearly move the two needles 32 at the same time.

The first actuator 33 is held by the actuator holder 34. The actuator holder 34 holds the first actuator 33 so as not to move forward and backward and so as not to rotate. The actuator holder 34 is configured such that the actuator holder 34 can be rotated together with the needles 32 and the first actuator 33 by a second actuator 37 described later.

The actuator holder 34 is disposed between the frames 30 when viewed from above, and is rotatably provided on each of the frames 30. More specifically, as shown in FIG. 5, the actuator holder 34 includes a pair of holding plates 35 provided between the first actuator 33 and the frames 30, and a pair of rotation shafts 36 respectively extending from each of the holding plates 35 to the corresponding frame 30. One of the rotation shafts 36 is rotatably supported by one of the frames 30, and the other rotation shaft 36 is rotatably supported by the other frame 30. The holding plates 35 are connected by a connecting member (not shown). The holding plates 35 and the rotation shafts 36 are integrally formed with each other.

As shown in FIG. 4, the two needles 32 are rotated by the second actuator 37 fixed to the frame 30. The second actuator 37 rotates the needle holder 32H via the actuator holder 34. Thus, the needles 32 are configured to rotate at the same time.

The second actuator 37 advances and retracts a pin 38 (engager) engaging with the actuator holder 34. More specifically, the pin 38 is held by a pin holder 38H, and the second actuator 37 holds and advances or retracts the pin 38 via the pin holder 38H. The locus of the forward and backward movement of the pin 38 is indicated by L1 in FIG. 4. Meanwhile, the actuator holder 34 includes a converter 39 with which the pin 38 is engaged. The converter 39 is configured to convert the forward and backward movement of the pin 38 into the rotational movement of the needles 32. The converter 39 is formed to extend upward from one holding plate 35 and is integrally formed with the holding plate 35.

In the present embodiment, the converter 39 includes a slot 40 into which the pin 38 is slidably engaged. The longitudinal direction of the slot 40 is orthogonal to the longitudinal direction of the needles 32. In the form shown in FIG. 4, the slot 40 extends in the vertical direction. In FIG. 5, the state in which the pin 38 engages with the slot 40 is shown by a cross section of the converter 39.

When viewed in the axial direction of the rotation shaft 36 of the actuator holder 34, the locus L1 of the forward and backward movement of the pin 38 by the second actuator 37 is spaced apart by a predetermined distance from the rotation center O of the rotation shaft 36 without passing through the rotation center O of the rotation shaft 36. As a result, when the pin 38 advances or retracts, the converter 39 of the actuator holder 34 receives the moment acting about the rotation center O of the rotation shaft 36 from the pin 38. For this reason, the actuator holder 34 rotates about the rotation center O together with the needles 32 and the first actuator 33. During this time, the pin 38 slides in the slot 40 of the actuator holder 34, whereby the distance from the rotation center O of the rotation shaft 36 is changed. The turning locus of the tip of each of the needles 32 is indicated by L2 in FIG. 4. In the embodiment shown in FIG. 4, there is shown an example in which the rotation center O of the rotation shaft 36 is disposed on the longitudinal extension line of the slot 40. However, the present disclosure is not limited thereto as long as the actuator holder 34 can smoothly rotate according to the forward and backward movement of the pin 38.

As shown in FIG. 4, the culture container linkage device 3 according to the present embodiment further includes a washing block 50 (washer) configured to wash the needles 32 and a sterilization block 70 (sterilizer) configured to sterilize the needles 32. The needles 32 may be advanced into or retracted from the washing block 50 and the sterilization block 70, respectively. Both the washing block 50 and the sterilization block 70 are attached to the frames 30.

Figure 6:
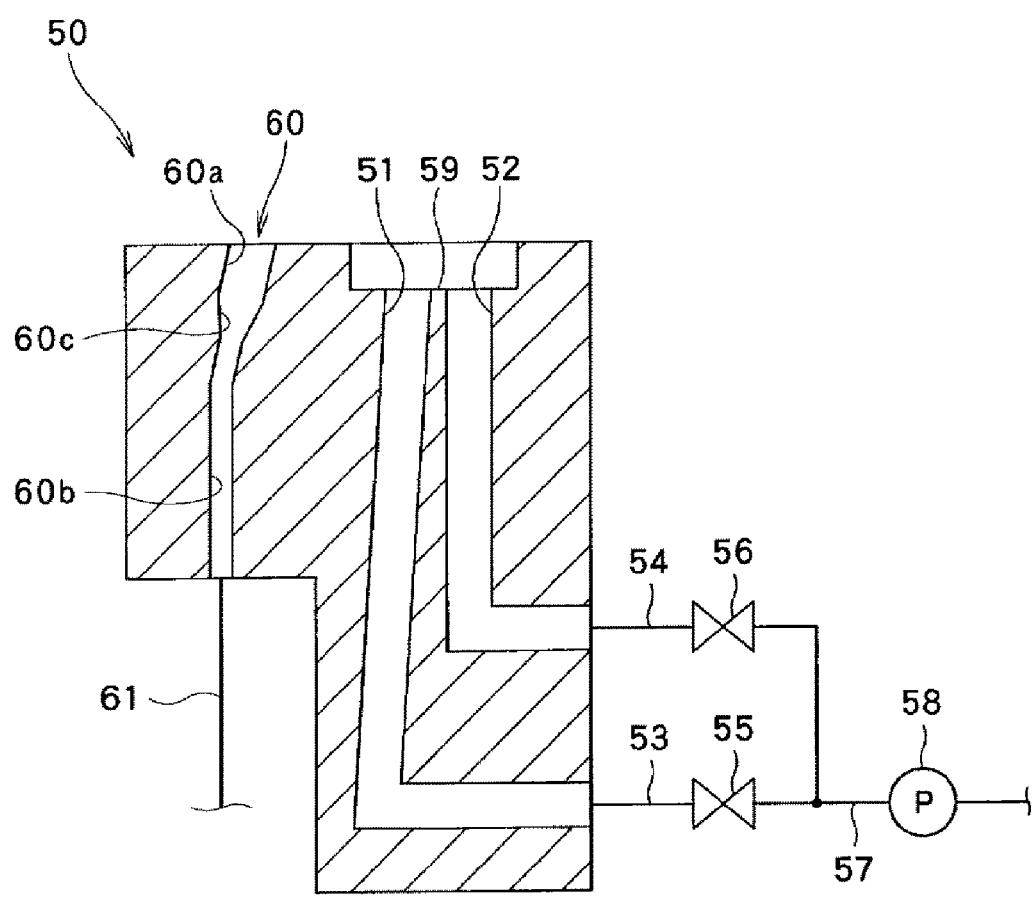
FIG. 6 is a sectional view showing a washing block of the culture container linkage device shown in FIG. 4.

As shown in FIG. 6, the washing block 50 includes two internal washing holes 51 for performing internal washing of the needles 32 and two external washing holes 52 for performing external washing of the needles 32. The internal washing holes 51 and the external washing holes 52 are formed such that the needles 32 can be advanced into or retreated from them. At least parts of the needles 32 are inserted into the internal washing holes 51 and the external washing holes 52. Among them, the external washing holes 52 are formed to extend in the vertical direction.

A first discharge line 53 is connected to the two internal washing holes 51, and the washing liquid in the two internal washing holes 51 is discharged to the first discharge line 53. A second discharge line 54 is connected to the two external washing holes 52, and the washing liquid in the two external washing holes 52 is discharged to the second discharge line 54. The first discharge line 53 is provided with a first discharge valve 55, and the second discharge line 54 is provided with a second discharge valve 56. The first discharge line 53 and the second discharge line 54 merge with a third discharge line 57 on the downstream side thereof. A discharge pump 58 (for example, a vacuum pump) is provided in the third discharge line 57. The washing liquid can be discharged by driving the discharge pump 58.

The two internal washing holes 51 are arranged side by side in the axial direction of the rotation shaft 36 of the actuator holder 34 and are arranged at the same interval as the inlet 103 and the outlet 105 of the culture container 100. The arrangement of the two external washing holes 52 is the same. As a result, the two needles 32 can be simultaneously inserted into the two internal washing holes 51 and can be simultaneously inserted into the two external washing holes 52. In FIG. 6, one of the two internal washing holes 51 and one of the two external washing holes 52 are shown, and the other internal washing hole 51 and the other external washing hole 52 are not shown.

Two concave communication passages 59 are provided on the upper surface of the washing block 50. Each of the communication passages 59 brings one internal washing hole 51 and one external washing hole 52 (into which the needle 32 inserted into the one internal washing hole 51 is inserted) corresponding to the one internal washing hole 51 into communication with each other. Each of the communication passages 59 guides the washing liquid overflowing from the external washing hole 52 to the internal washing hole 51.

As shown in FIG. 6, the washing block 50 further includes two bypass holes 60 (bypass parts) communicating with each other. The bypass holes 60 are formed such that the needles 32 can be advanced into or retracted from them. At least parts of the needles 32 are inserted into the bypass holes 60. The arrangement of the two bypass holes 60 is similar to the arrangement of the two internal washing holes 51 described above such that the two needles 32 can be inserted into the two bypass holes 60 at the same time. In FIG. 6, one of the bypass holes 60 is not shown.

The two bypass holes 60 are in communication with each other via a bypass line 61. That is, the bypass hole 60 corresponding to the first needle 32a described above is in communication with the bypass hole 60 corresponding to the second needle 32b via the bypass line 61. As a result, when each of the needles 32a and 32b is inserted into the corresponding bypass hole 60, the first needle 32a and the second needle 32b communicate with each other through the two bypass holes 60 and the bypass line 61. Therefore, the culture medium supplied to the first needle 32a can be supplied to the second needle 32b via the bypass hole 60 corresponding to the first needle 32a, the bypass line 61 and the bypass hole 60 corresponding to the second needle 32b. The culture medium supplied to the second needle 32b is collected in the culture medium analyzer 4 (see FIG. 1). The bypass hole 60 corresponding to the first needle 32a communicates with an additional line (not shown) different from the bypass line 61. The additional line may be directly or indirectly connected to the culture medium analyzer 4. Also in this case, the new culture medium supplied to the first needle 32a can be collected in the culture medium analyzer 4.

Meanwhile, the tip end of the needle 32 inserted into the bypass hole 60 can make contact with the wall surface of the bypass hole 60. More specifically, the bypass hole 60 includes a large diameter hole portion 60a provided on the side of the needle 32, a small diameter hole portion 60b provided on the side of the bypass line 61, and a tapered hole portion 60c provided between the large diameter hole portion 60a and the small diameter hole portion 60b. Among them, the small diameter hole portion 60b has a diameter smaller than that of the large diameter hole portion 60a. The large diameter hole portion 60a and the tapered hole portion 60c are formed along the longitudinal direction of the needle 32 inserted into the bypass hole 60. The portion of the small diameter hole portion 60b on the side of the tapered hole portion 60c is formed along the longitudinal direction of the needle 32, but the portion of the small diameter hole portion 60b on the side of the bypass line 61 is formed along the vertical direction. That is, the small diameter hole portion 60b is formed to be bent. Meanwhile, the needle 32 includes a tapered portion 32T (see FIG. 10) provided at its tip. As a result, when the needle 32 is inserted into the bypass hole 60, the tapered portion 32T of the needle 32 receives the driving force of the first actuator 33, whereby the tapered portion 32T of the needle 32 is brought into contact with and pressed against the wall surface of the tapered hole portion 60c of the bypass hole 60. Thus, the culture medium discharged from the tip of the first needle 32a is prevented from flowing out to the side of the large diameter hole portion 60a. In addition, the culture medium supplied from the bypass line 61 can flow smoothly into the second needle 32b, and the outflow of the culture medium to the side of the large diameter hole portion 60a is suppressed. In order to effectively suppress the outflow of the culture medium, it may be preferable that the washing block 50 is made of a resin (e.g., polyether ether ketone (PEEK)) and the needle 32 is made of stainless steel (e.g., SUS316L).

As shown in FIG. 4, the sterilization block 70 has two sterilization holes 71 for sterilizing the needles 32. The sterilization holes 71 are formed such that the needles 32 can be advanced into or retracted from them. At least parts of the needles 32 are inserted into the sterilization holes 71. The sterilization block 70 includes a heater (not shown) that heats the needles 32 inserted into the sterilization holes 71. At the time of sterilization, the needles 32 are heated to about 200 degrees C. The arrangement of the two sterilization holes 71 is the same as the arrangement of the two internal washing holes 51 described above, such that the two needles 32 can be simultaneously inserted into the two sterilization holes 71. In FIG. 6, one of the sterilization holes 71 is not shown.

As shown in FIG. 4, the container holder 31, the washing block 50 and the sterilization block 70 described above are arranged at different positions in the rotation direction of the needle 32 on the outer peripheral side of the rotation locus L2 of the needle 32 with respect to the rotation center O. In the present embodiment, the container holder 31, the sterilization block 70 and the washing block 50 are arranged such that the mounting height to the frame 30 decreases in this order.

In the washing block 50, the internal washing hole 51, the external washing hole 52 and the bypass hole 60 are disposed at different positions in the rotation direction of the needle 32. In the present embodiment, the bypass hole 60, the internal washing hole 51 and the external washing hole 52 are disposed so as to become distant from the container holder 31 and the sterilization block 70 in this order.

The needle 32 may be positioned, by the second actuator 37, at a container-facing position P1 at which the needles 32 face the inlet 103 and the outlet 105 of the culture container 100 held in the container holder 31 and a washing-facing position P2 or P3 at which the needles 32 face the washing block 50. When the needles 32 are positioned at the container-facing position P1, the two needles 32 are respectively aligned with the inlet 103 and the outlet 105 of the culture container 100 in the longitudinal direction thereof. In the embodiment shown in FIG. 4, the needles 32 are disposed horizontally at the container-facing position P1. Then, when advanced by the first actuator 33 (linearly moved toward the inlet 103 and the outlet 105), the two needles 32 simultaneously penetrate the inlet rubber plug 108 and the outlet rubber plug 109. Thus, the two needles 32 are inserted into the culture container 100.

The washing-facing position includes an internal washing-facing position P2 at which the needles 32 face the internal washing holes 51 and an external washing-facing position P3 at which the needles 32 face the external washing holes 52. That is, the needles 32 may be positioned at the internal washing-facing position P2 and the external washing-facing position P3. When the needles 32 are positioned at the internal washing-facing position P2, the two needles 32 are respectively aligned with the corresponding internal washing holes 51 in the longitudinal direction thereof. Then, when advanced by the first actuator 33, the two needles 32 are simultaneously inserted into the two internal washing holes 51. When the needles 32 are positioned at the external washing-facing position P3, the two needles 32 are respectively aligned with the corresponding external washing holes 52 in the longitudinal direction thereof. In the embodiment shown in FIG. 4, the longitudinal direction of the needles 32 is vertical at the external washing-facing position P3. Then, when advanced by the first actuator 33, the two needles 32 are simultaneously inserted into the two external washing holes 52.

Furthermore, the needles 32 may be positioned, by the second actuator 37, at a bypass-facing position P4 at which the needles 32 face the bypass holes 60 of the washing block 50. When the needles 32 are positioned at the bypass-facing position P4, the two needles 32 are respectively aligned with the corresponding bypass holes 60 in the longitudinal direction thereof. Then, when advanced by the first actuator 33, the two needles 32 are simultaneously inserted into the two bypass holes 60.

Furthermore, the needles 32 may be positioned, by the second actuator 37, at a sterilization-facing position P5 at which the needles 32 face the sterilization holes 71 of the sterilization block 70. When the needles 32 are positioned at the sterilization-facing position P5, the two needles 32 are respectively aligned with the corresponding sterilization holes 71 of the sterilization block 70 in the longitudinal direction thereof. Then, when advanced by the first actuator 33, the two needles 32 are simultaneously inserted into the two sterilization holes 71.

The first actuator 33 and the second actuator 37 are connected to the controller 20 described above. The controller 20 is configured to control the first actuator 33 and the second actuator 37.

Next, the operation (the needle washing method) of the present embodiment having such a configuration will be described.

At the time of culture medium replacement, as shown in FIG. 4, first, the needles 32 are rotated by the second actuator 37 and positioned at the container-facing position P1. As a result, the two needles 32 are respectively aligned with the inlet 103 and the outlet 105 of the culture container 100 (see FIG. 2) held by the container holder 31.

Subsequently, the needles 32 are advanced from the container-facing position P1 to the inlet 103 and the outlet 105 by the first actuator 33. The needles 32 pierce and penetrate the inlet rubber plug 108 and the outlet rubber plug 109. As a result, the needles 32 are simultaneously inserted into the inlet 103 and the outlet 105, whereby the new solution buffer tank 6 (see FIG. 1) and the inlet 103 are connected to each other and the outlet 105 and the culture medium analyzer 4 are connected to each other.

Thereafter, the outlet pump 11 is driven such that the old culture medium is withdrawn from the passage 104 of the culture container 100 via the second needle 32b and supplied to the culture medium analyzer 4. At this time, the new culture medium stored in the new solution buffer tank 6 flows into the passage 104 through the first needle 32a and the inlet 103 of the culture container 100. The old culture medium existing in the passage 104 is discharged as the old culture medium is pushed out by the new culture medium. Thus, the culture medium existing in culture container 100 is replaced.

After the culture medium replacement, the needles 32 are retracted and removed from the inlet rubber plug 108 and the outlet rubber plug 109 by the first actuator 33. The respective rubber plugs 108 and 109 from which the needles 32 have been retracted closes the inlet 103 and the outlet 105 again due to the elasticity of the material thereof. The retracted needles 32 are positioned again at the container-facing position P1.

After being positioned at the container-facing position P1, the needles 32 are rotated by the second actuator 37 and subjected to internal washing in the washing block 50.

In this case, first, as shown in FIG. 4, the two needles 32 are rotated from the container-facing position P1 and positioned at the internal washing-facing position P2. The two needles 32 are respectively aligned with the corresponding internal washing holes 51 of the washing block 50.

Figure 7:
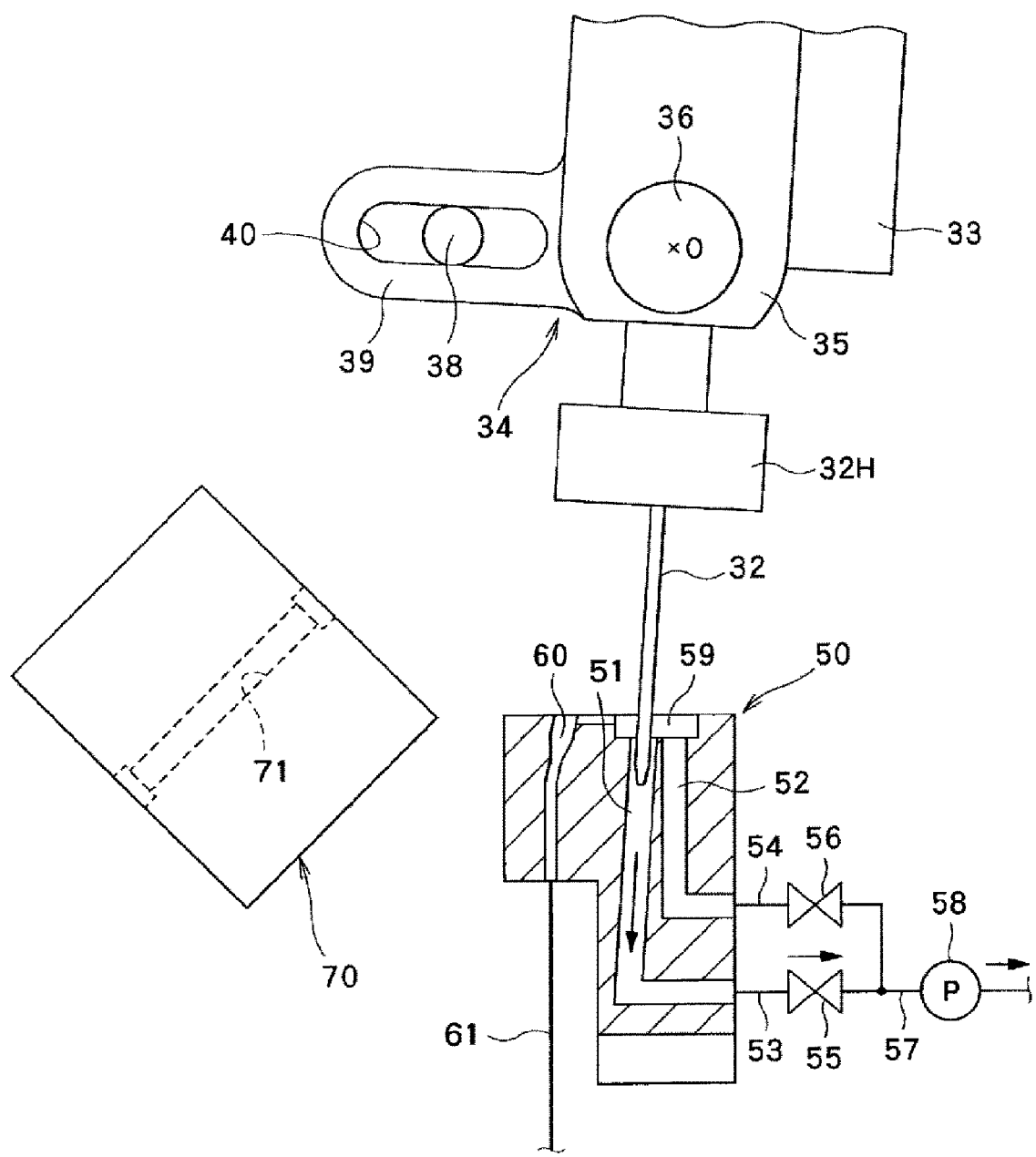
FIG. 7 is a sectional view showing the needle at the time of internal washing in the method for washing the needle of the culture container linkage device shown in FIG. 4.

Subsequently, the needles 32 are advanced from the internal washing-facing position P2 toward the corresponding internal washing holes 51 by the first actuator 33. As shown in FIG. 7, the needles 32 are inserted into the internal washing holes 51.

Next, the inlet washing pump 16 is driven, the inlet washing opening/closing valve 17 is opened, and the washing liquid is supplied from the inlet washing liquid supply source 14 to the first needle 32a via the inlet heater 5 and the new solution buffer tank 6. On the other hand, the outlet washing pump 18 is driven, the outlet washing opening/closing valve 19 is opened, and the outlet opening/closing valve 13 is closed. As a result, the washing liquid is supplied from the outlet washing liquid supply source 15 to the second needle 32b via the outlet pump 11. In this case, the washing liquid flows through the outlet pump 11 in the direction opposite to the direction in which the culture medium flows during the culture medium replacement.

During the internal washing of the needles 32, the discharge pump 58 is driven and the first discharge valve 55 provided in the first discharge line 53 is opened. As a result, the washing liquid supplied to each needle 32 is discharged from the tip of each needle 32 through the internal flow path of the needle 32. The discharged washing liquid is discharged to the third discharge line 57 via the first discharge line 53. During this time, the washing liquid passes through the internal flow path of each needle 32, whereby the internal flow path is washed with the washing liquid (the needle 32 is subjected to internal washing).

After the internal washing, the inlet washing pump 16 and the outlet washing pump 18 are stopped, and the inlet washing opening/closing valve 17 and the outlet washing opening/closing valve 19 are closed. Then, the needles 32 are retracted from the internal washing holes 51 by the first actuator 33, pulled out from the internal washing holes 51, and positioned again at the internal washing-facing position P2.

After being positioned at the internal washing-facing position P2, the needles 32 are rotated by the second actuator 37 and subjected to external washing in the washing block 50.

In this case, first, as shown in FIG. 4, the two needles 32 are rotated from the internal washing-facing position P2 and positioned at the external washing-facing position P3, whereby the two needles 32 are respectively aligned with the corresponding external washing holes 52 of the washing block 50.

Figure 8:
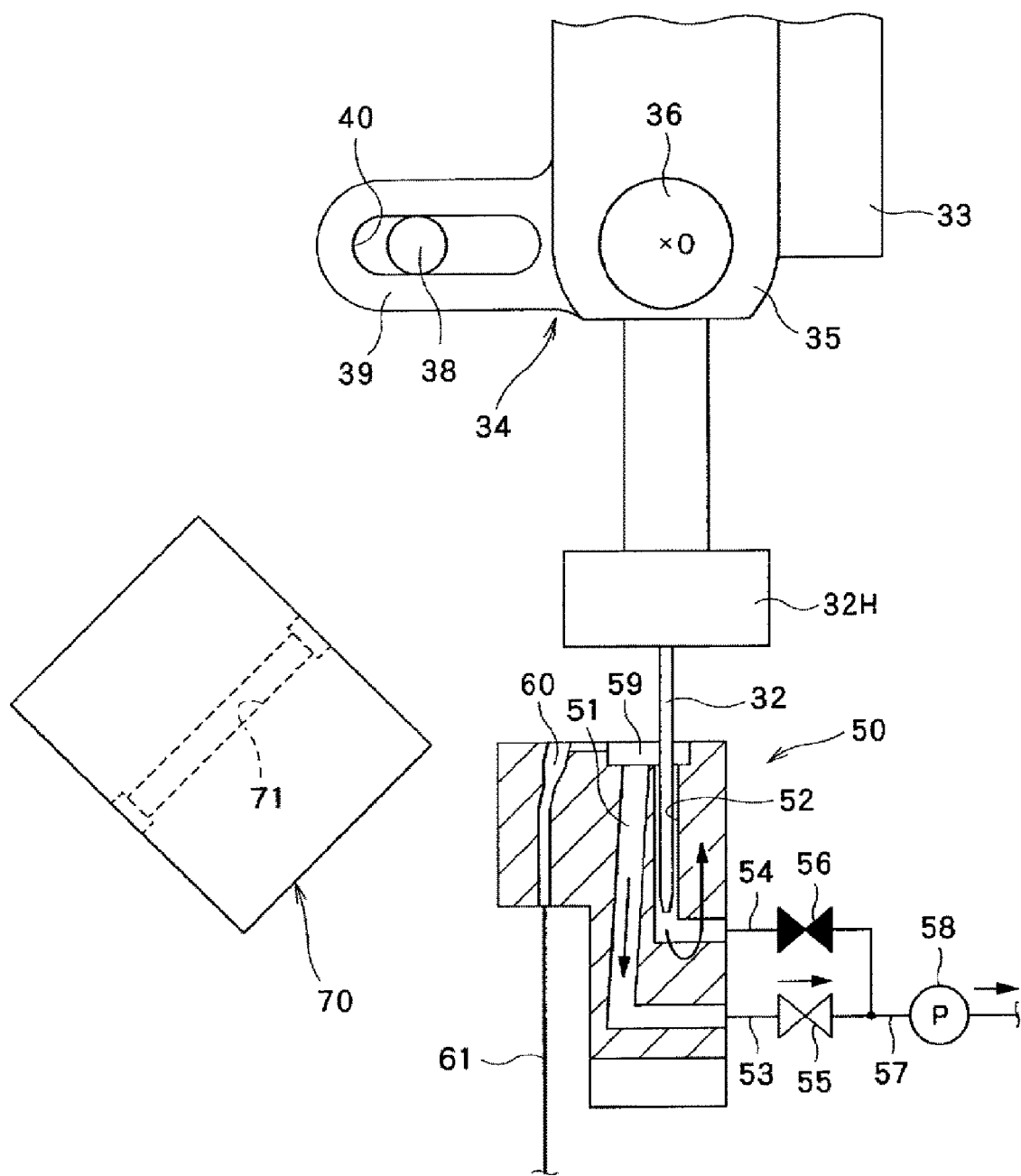
FIG. 8 is a sectional view showing the needle at the time of external washing in the method for washing the needle of the culture container linkage device shown in FIG. 4.

Subsequently, the needles 32 are advanced from the external washing-facing position P3 toward the corresponding external washing holes 52 by the first actuator 33, and are inserted into the external washing holes 52 as shown in FIG. 8. At this time, the insertion depth of the needles 32 into the external washing holes 52 is preferably larger than the insertion depth of the needles 32 into the internal washing holes 51. Moreover, it may be preferable that the insertion depth of the needles 32 into the external washing holes 52 is larger than the insertion depth of the needles 32 inserted into the inlet 103 and the outlet 105 of the culture container 100 at the time of culture medium replacement.

Next, as in the internal washing, the pumps 16 and 18 are driven and the washing opening/closing valves 17 and 19 are opened. Moreover, the outlet opening/closing valve 13 is closed. As a result, the washing liquid is supplied from the inlet washing liquid supply source 14 to the first needle 32a, and the washing liquid is supplied from the outlet washing liquid supply source 15 to the second needle 32b.

During the external washing of the needles 32, the discharge pump 58 is driven, the first discharge valve 55 is opened, and the second discharge valve 56 is closed. As a result, the washing liquid supplied to the respective needles 32 is discharged from the tip and accumulated in the external washing holes 52. The external washing holes 52 are filled with the washing liquid and the outer surfaces of the respective needles 32 are washed with the washing liquid 32 (The needles 32 are subjected to external washing).

The washing liquid overflowing from the external washing holes 52 flows to the corresponding internal washing holes 51 through the communication passage 59 provided on the upper surface of the washing block 50. The washing liquid reaching the internal washing holes 51 is discharged to the third discharge line 57 via the first discharge line 53. Since the second discharge valve 56 is closed during the external washing, it is possible to prevent bacteria from entering the external washing holes 52 from the downstream side (from the side of the discharge pump 58) and to improve the cleanliness of the external washing holes 52. In addition, during the external washing, the external washing holes 52 themselves are also washed. Meanwhile, when the first discharge valve 55 is closed, the second discharge valve 56 is opened, and the discharge pump 58 is driven to discharge the washing liquid with the needles 32 inserted into the internal washing holes 51, it is possible to cause the washing liquid to overflow from the internal washing holes 51 and to wash the internal washing holes 51 themselves.

After the external washing, the pumps 16 and 18 are stopped and the washing opening/closing valves 17 and 19 are closed. Furthermore, the second discharge valve 56 is opened, whereby the washing liquid staying in the external washing holes 52 is discharged to the second discharge line 54. Then, the needles 32 are retracted from the external washing holes 52 by the first actuator 33, withdrawn from the external washing holes 52, and positioned again at the external washing-facing position P3.

After being positioned at the external washing-facing position P3, the needles 32 are rotated by the second actuator 37 and sterilized in the sterilization block 70.

In this case, first, as shown in FIG. 4, the two needles 32 are rotated from the external washing-facing position P3 and positioned at the sterilization-facing position P5, whereby the two needles 32 are respectively aligned with the corresponding sterilization holes 71 of the sterilization block 70.

Figure 9:
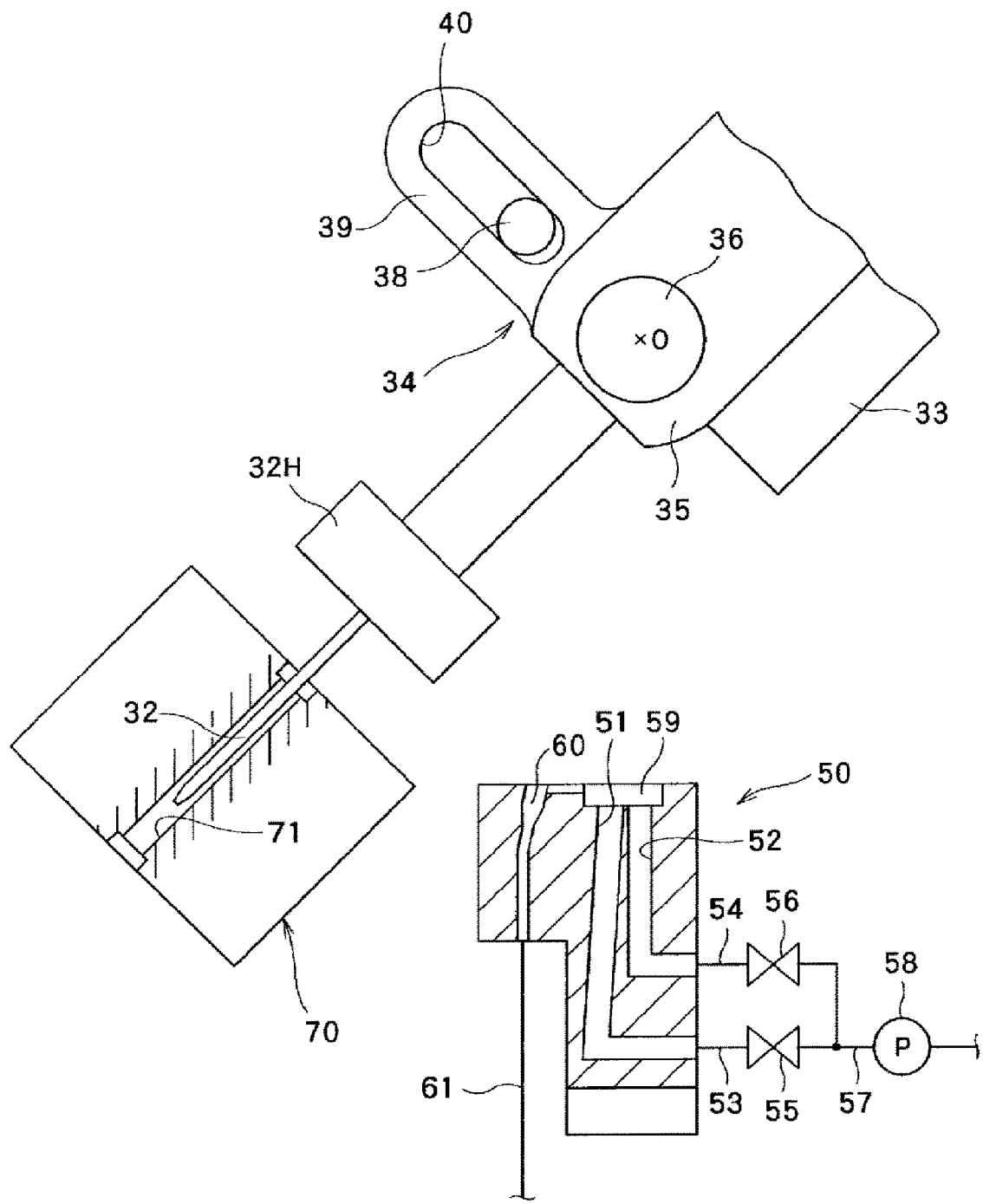
FIG. 9 is a sectional view showing the needle at the time of sterilization in the method for washing the needle of the culture container linkage device shown in FIG. 4.

Subsequently, the needles 32 are advanced from the sterilization-facing position P5 toward the corresponding sterilization holes 71 by the first actuator 33 and are inserted into the sterilization holes 71 as shown in FIG. 9. At this time, the insertion depth of the needles 32 into the sterilization holes 71 is preferably larger than the insertion depth of the needles 32 inserted into the inlet 103 and the outlet 105 of the culture container 100 at the time of container medium replacement.

Next, the heater of the sterilization block 70 is driven to heat and sterilize the needles 32 inserted into the sterilization holes 71.

After the sterilization, the heater is stopped, and the needles 32 are retracted from the sterilization holes 71 by the first actuator 33, withdrawn from the sterilization holes 71 and positioned again at the sterilization-facing position P5.

When the components of a new culture medium are analyzed after sterilization, the needles 32 are rotated from the sterilization-facing position P5 by the second actuator 37 and are positioned at the bypass-facing position P4 as shown in FIG. 4. Thus, the two needles 32 are respectively aligned with the corresponding bypass holes 60 of the washing block 50.

Figure 10:
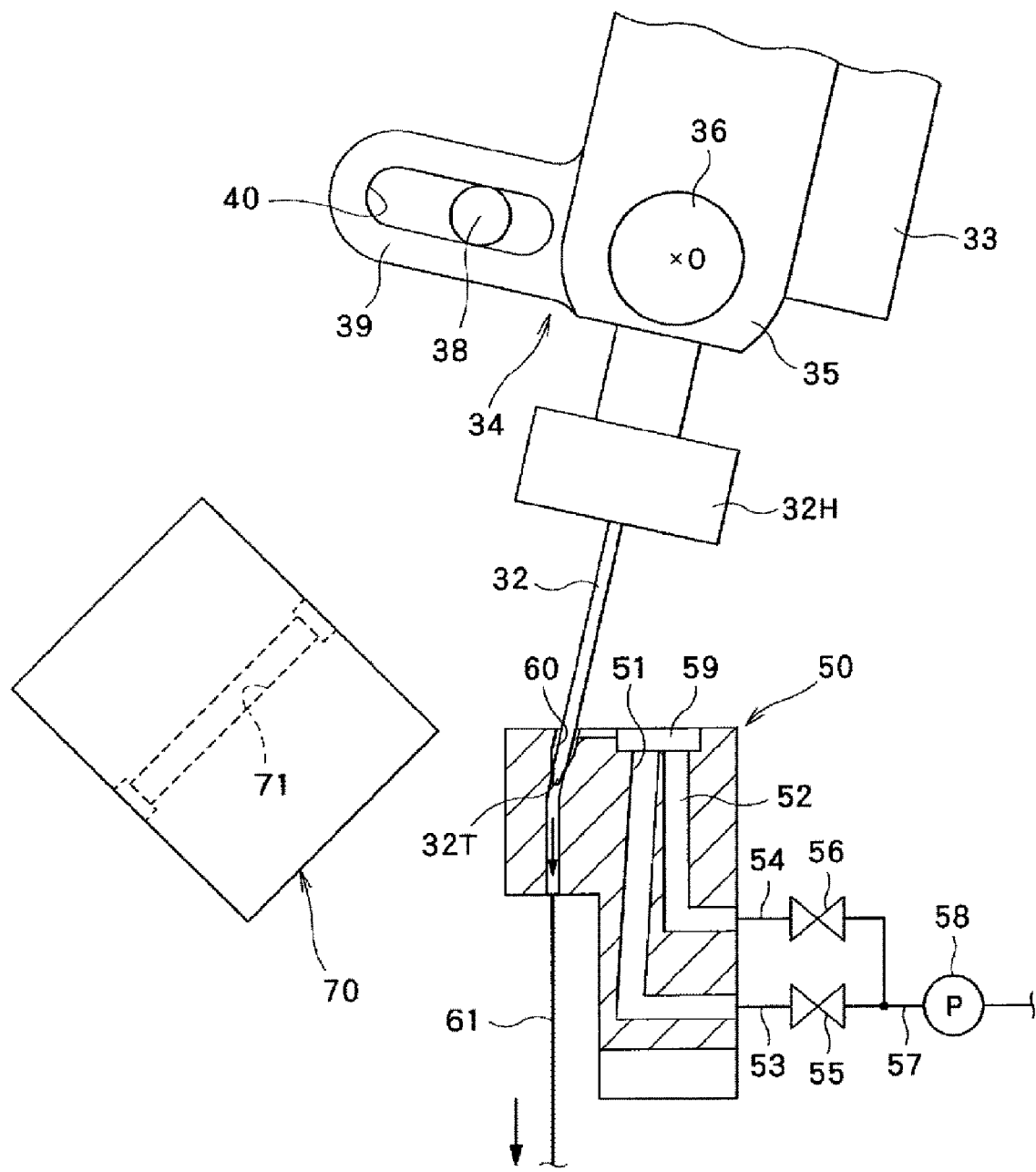
FIG. 10 is a sectional view showing the needle at the time of bypassing in the method for washing the needle of the culture container linkage device shown in FIG. 4.

Subsequently, the needles 32 are advanced from the bypass-facing position P4 toward the corresponding bypass holes 60 by the first actuator 33 and are inserted into the bypass holes 60 as shown in FIG. 10. In this case, the first needle 32a and the second needle 32b are respectively inserted into the corresponding bypass holes 60. The first needle 32a and the second needle 32b are communicated with each other through the two bypass holes 60 and the bypass line 61.

Next, the second inlet opening/closing valve 9 is opened, and a new culture medium is supplied from the new solution buffer tank 6 to the first needle 32a. The supplied culture medium is discharged from the tip of the first needle 32a, and the discharged culture medium is supplied to the second needle 32b via the bypass hole 60 into which the first needle 32a is inserted, the bypass line 61, and the bypass hole 60 into which the second needle 32b is inserted. The culture medium supplied to the second needle 32b is collected in the culture medium analyzer 4. That is, the new culture medium is collected in the culture medium analyzer 4 without passing through the culture container 100. The collected culture medium is subjected to component analysis in the culture medium analyzer 4.

After the recovery of the culture medium for analysis, the second inlet opening/closing valve 9 is closed. Then, the two needles 32 are retracted from the bypass holes 60 by the first actuator 33, withdrawn from the bypass holes 60, and positioned again at the bypass-facing position P4.

As described above, according to the present embodiment, the needles 32 for replacing the culture medium present in the culture container 100 can be positioned, by the second actuator 37, at the washing-facing positions P2 and P3 facing the washing block 50. The needles 32 can be advanced into the washing block 50 by the first actuator 33. As a result, the needles 32 after culture medium replacement can be washed by advancing them to the washing block 50, which makes it possible to eliminate the need to replace needles 32. Accordingly, it is possible to improve the efficiency of the culture medium replacement operation.

Furthermore, according to the present embodiment, the pin 38 moved forward and backward by the second actuator 37 engages with the converter 39 of the actuator holder 34. The forward and backward movement of the pin 38 is converted into the rotational movement of the needles 32. Thus, the structure for rotating the needles 32 can be made compact. Therefore, the space occupied by the culture container linkage device 3 in the sterilization chamber 10 can be reduced. Furthermore, the mechanism for washing the needles 32 after culture medium replacement can be realized by the two actuators 33 and 37, which makes it possible to prevent the structure from becoming complex. Accordingly, it is possible to simplify the culture container linkage device 3.

Furthermore, according to the present embodiment, the pin 38 engages with and slides along the slot 40 of the converter 39 of the actuator holder 34. Thus, the forward and backward movement of the pin 38 can be smoothly converted into the rotational movement of the needles 32. Accordingly, the loss of power of the second actuator 37 can be reduced, and the needles 32 can be smoothly rotated.

Furthermore, according to the present embodiment, the washing block 50 has the internal washing holes 51 and the external washing holes 52. The needles 32 positioned at the internal washing-facing position P2 can be inserted into the internal washing holes 51. The needles 32 positioned at the external washing-facing position P3 can be inserted into the external washing holes 52. As a result, the internal washing of the needles 32 can be performed in the internal washing holes 51, and the external washing of the needles 32 can be performed in the external washing holes 52. Accordingly, it is possible to further enhance the washing effect of the needles 32.

Furthermore, according to the present embodiment, the washing block 50 has the bypass holes 60, and the needles 32 positioned at the bypass-facing position P4 can be inserted into the bypass holes 60. As a result, the new culture medium discharged from the first needle 32a can be collected in the culture medium analyzer 4 via the bypass line 61 and the second needle 32b, and the components of the collected new culture medium can be efficiently analyzed.

Furthermore, according to the present embodiment, the needles 32 for replacing the culture medium present in the culture container 100 can be positioned, by the second actuator 37, at the sterilization-facing position P5 facing the sterilization block 70 and can be advanced into the sterilization block 70 by the first actuator 33. As a result, the washed needles 32 can be sterilized in the sterilization block 70. Accordingly, it is possible to prevent bacteria from adhering to the needles 32 and to further disinfect the needles 32.

In the present embodiment described above, there has been described an example in which the culture container linkage device 3 includes the sterilization block 70. However, the present disclosure is not limited thereto. The sterilization block 70 may not be provided.

Furthermore, in the above-described embodiment, there has been described an example in which the washing block 50 has the bypass holes 60 (bypass parts) for recovering the culture medium for component analysis. However, the present disclosure is not limited thereto. The bypass holes 60 may be provided in a block different from the washing block 50, as long as the bypass holes 60 are disposed at different positions in the rotation direction of the needles 32 with respect to the washing block 50 and the sterilization block.

Second Embodiment

Next, a culture container linkage device and a method for washing a needle according to a second embodiment of the present disclosure will be described with reference to FIGS. 11 and 12.

Figure 11:
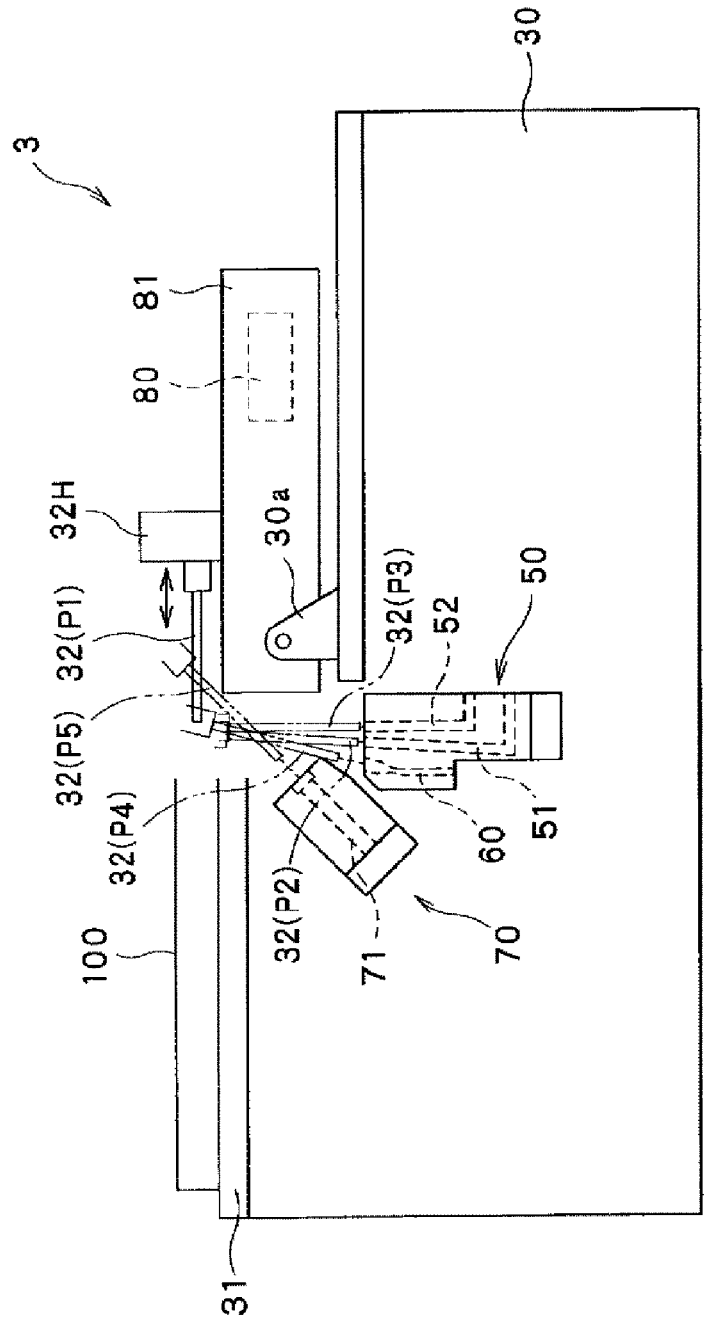
FIG. 11 is a schematic configuration view showing a culture container linkage device according to a second embodiment.
Figure 12:
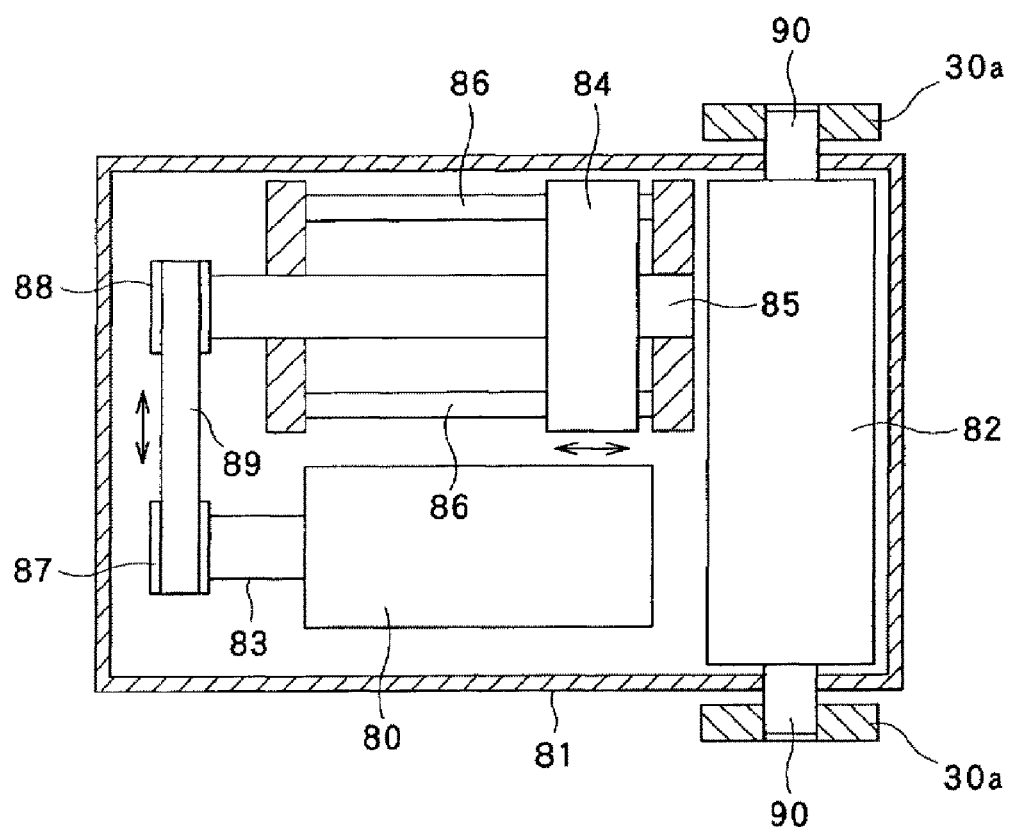
FIG. 12 is a schematic plan view showing the culture container linkage device shown in FIG. 11.

The second embodiment shown in FIGS. 11 and 12 is mainly different from the first embodiment shown in FIGS. 1 to 10 in that the second actuator is held by the actuator holder and the needles can be rotated by rotating the actuator holder with a reaction force against the frame. The other configurations are substantially the same as those of the first embodiment shown in FIGS. 1 to 10. In FIGS. 11 and 12, the same parts as those of the first embodiment shown in FIGS. 1 to 10 are designated by the same reference numerals and the detailed description thereof will be omitted.

As shown in FIGS. 11 and 12, in the present embodiment, the two needles 32 can be advanced and retracted by a first actuator 80. The first actuator 80 is held by an actuator holder 81 rotatably provided on the support part 30a of the frame 30. The needles 32 are rotatable by a second actuator 82 via the actuator holder 81.

In the present embodiment, the second actuator 82 is held by the actuator holder 81. That is, the actuator holder 81 according to the present embodiment is formed in a case shape so as to accommodate and hold the first actuator 80 and the second actuator 82. The needle holder 32H is attached to the actuator holder 81 so as to be linearly movable.

As shown in FIG. 12, the first actuator 80 includes a rotation shaft 83 and is configured to rotationally drive the rotation shaft 83. For example, a stepping motor may be suitably used as the first actuator 80. Meanwhile, a nut 84 is connected to the needle holder 32H. The nut 84 is threadedly coupled to a threaded shaft 85 (for example, a slide screw, a ball screw, etc.) having an external thread formed on the outer peripheral surface thereof. The threaded shaft 85 is rotatably held in the actuator holder 81. The rotation shaft 83 and the threaded shaft 85 of the first actuator 80 are arranged in parallel with each other. Furthermore, guide rods 86 extending in parallel to the threaded shaft 85 are provided on both sides of the threaded shaft 85. These guide rods 86 guide the linear movement of the nut 84. The nut 84 can be linearly moved by the rotation of the threaded shaft 85.

A first pulley 87 is provided at an end portion of the rotation shaft 83. On the other hand, a second pulley 88 is provided at an end portion of the threaded shaft 85. A timing belt 89 is wound around the first pulley 87 and the second pulley 88. The rotation of the first pulley 87 is transmitted to the second pulley 88 via the timing belt 89. Thus, the rotational driving force of the first actuator 80 is transmitted to the threaded shaft 85, and the needles 32 held by the needle holder 32H are configured to linearly move.

The second actuator 82 includes a rotation shaft 90 non-rotatably fixed to the frame 30. The rotation shaft 90 is formed to penetrate the main body of the second actuator 82. For example, a stepping motor may be suitably used as the second actuator 82.

The second actuator 82 is configured to rotate the needles 32 via the actuator holder 81 by rotating the actuator holder 81 with a reaction force against the frame 30. That is, since the rotation shaft 90 is non-rotatably fixed to the frame 30, when the second actuator 82 is driven, the rotation shaft 90 is not rotated but the second actuator 82 is rotated with respect to the rotation shaft 90 by a reaction force. In this case, the actuator holder 81 holding the second actuator 82 is rotated with respect to the frame 30, whereby the needles 32 are rotated.

The first actuator 80 and the second actuator 82 as described above are controlled by the above-described controller 20 in the same manner as the first actuator 33 and the second actuator 37 of the first embodiment. That is, the two needles 32 may be positioned, by the second actuator 82, at the container-facing position P1, the washing-facing positions P2 and P3, the bypass-facing position P4 and the sterilization-facing position P5. When the needles 32 are positioned at the container-facing position P1, the needles 32 may be advanced and retracted with respect to the culture container 100 by the first actuator 80. When the needles 32 are positioned at the internal washing-facing position P2, the needles 32 may be advanced and retracted with respect to the internal washing holes 51 by the first actuator 80. When the needles 32 are positioned at the external washing-facing position P3, the needles 32 may be advanced and retracted with respect to the external washing holes 52 by the first actuator 80. When the needles 32 are positioned at the bypass-facing position P4, the needles 32 may be advanced and retracted with respect to the bypass holes 60 by the first actuator 80. When the needles 32 are positioned at the sterilization-facing position P5, the needles 32 may be advanced and retracted with respect to the sterilization holes 71 by the first actuator 80.

As described above, according to the present embodiment, the second actuator 82 held by the actuator holder 81 can rotate the actuator holder 81 with the reaction force against the frame 30 and can rotate the needles 32 via the actuator holder 81. As a result, the structure for rotating the needles 32 can be made compact. Therefore, it is possible to reduce the space occupied by the culture container linkage device 3 in the sterilization chamber 10. Furthermore, the mechanism for washing the needles 32 after container medium replacement can be realized by the two actuators 80 and 82, which makes it possible to prevent the structure from becoming complex. In particular, it is possible to simplify the mechanism for transmitting the rotational driving force from the second actuator 82 to the needles 32. Therefore, it is possible to simplify the culture container linkage device 3. In addition, since the actuator holder 81 accommodates the first actuator 80 and the second actuator 82, it is possible to make more compact the structure for rotating the needles 32.

The present disclosure is not limited to the above embodiments and modifications thereof. At the implementation stage, the constituent elements may be modified and embodied without departing from the scope of the present disclosure. In addition, various inventions may be made by appropriate combinations of the constituent elements disclosed in the above-described embodiments and modifications. Some components may be deleted from all the components shown in the embodiments and modifications. In addition, components in different embodiments and modifications may be combined as appropriate.

What is claimed is:

1. A culture container linkage device, to which a culture container is linked when a culture medium is replaced, comprising:
  a frame;
  a container holder provided on the frame and configured to hold the culture container;
  two needles held by a needle holder and configured to be advanced into or retreated from the culture container held by the container holder, the culture medium in the culture container being replaced by the needles;
a first actuator configured to advance or retract the needles;
an actuator holder rotatably provided on the frame and configured to hold the first actuator;
a second actuator configured to rotate the needles via the actuator holder; and
a washer provided such that the needles are advanced into or retreated from the washer, and configured to wash the needles,
wherein the container holder and the washer are disposed at different positions in a rotation direction of the needles, and wherein the needles are configured to be positioned, by the second actuator, at a container-facing position at which the needles face the culture container held by the container holder and a washing-facing position at which the needles face the washer.

2. The culture container linkage device of claim 1, further comprising an engager configured to engage with the actuator holder,
wherein the second actuator is configured to move the engager forward and backward while holding the engager, and
wherein the actuator holder includes a converter engaged with the engager and configured to convert a forward-backward movement of the engager into a rotational movement of the needles.

3. The culture container linkage device of claim 1, wherein the second actuator is held by the actuator holder, and
wherein the second actuator includes a rotation shaft non-rotatably fixed to the frame, and is configured to rotate the needles via the actuator holder by rotating the actuator holder with a reaction force against the frame.

4. The culture container linkage device of claim 1, wherein the washer includes:
an internal washing hole provided such that the needles are advanced into or retracted from the internal washing hole, and configured to perform internal washing of the needles; and
an external washing hole provided such that the needles are advanced into or retracted from the external washing hole, and configured to perform external washing of the needles,
wherein the internal washing hole and the external washing hole are disposed at different positions in the rotation direction of the needles,
wherein the washing-facing position includes an internal washing-facing position at which the needles face the internal washing hole and an external washing-facing position at which the needles face the external washing hole, and
wherein the needles are configured to be positioned, by the second actuator, at the internal washing-facing position and the external washing-facing position.

5. The culture container linkage device of claim 1, further comprising a bypass part provided such that the needles are advanced into or retracted from the bypass part, and configured to bring the needles into communication with each other,
wherein the bypass part is disposed at a position different from the positions of the container holder and the washer in the rotation direction of the needles, and
wherein the needles are configured to be positioned, by the second actuator, at a bypass-facing position at which the needles face the bypass part.

6. The culture container linkage device of claim 1, further comprising a sterilizer provided such that the needles are advanced into or retracted from the sterilizer, and configured to sterilize the needles,
wherein the sterilizer is disposed at a position different from the positions of the container holder and the washer in the rotation direction of the needles, and
wherein the needles are configured to be positioned, by the second actuator, at a sterilization-facing position at which the needles face the sterilizer.

7. A culture system comprising:
the culture container linkage device of claim 1;
a buffer tank configured to store a new culture medium; and
a culture medium discharge driver configured to discharge the culture medium from the culture container held by the container holder of the culture container linkage device,
wherein one of the needles of the culture container linkage device is connected to the buffer tank, and the other of the needles is connected to the culture medium discharge driver.

8. A method for washing two needles of a culture container linkage device to be linked to a culture container when a culture medium is replaced, comprising:
inserting the needles into the culture container and replacing the culture medium in the culture container;
positioning the needles at a container-facing position at which the needles face the culture container, by retracting the needles from the culture container; and
positioning the needles at a washing-facing position at which the needles face a washer for washing the needles, by rotating the needles from the container-facing position, advancing the needles from the washing-facing position, and washing the needles in the washer.

9. The method of claim 8, wherein the culture container linkage device includes a first actuator, an actuator holder configured to hold the first actuator, and a second actuator configured to rotate the actuator holder,
wherein the needles are advanced and retracted by the first actuator, and
wherein the needles are rotated by the second actuator.

10. The method of claim 9, wherein the culture container linkage device further includes an engager configured to engage with the actuator holder,
wherein the second actuator is configured to move the engager forward and backward while holding the engager, and
wherein the actuator holder includes a converter engaged with the engager and configured to convert a forward-backward movement of the engager into a rotational movement of the needles.

11. The method of claim 9, wherein the culture container linkage device further includes a frame on which the actuator holder is rotatably provided,
wherein the second actuator is held by the actuator holder, and
wherein the second actuator includes a rotation shaft non-rotatably fixed to the frame, and is configured to rotate the needles via the actuator holder by rotating the actuator holder with a reaction force against the frame.

12. The method of claim 8, wherein the washer includes an internal washing hole configured to perform internal washing of the needles, and an external washing hole configured to perform external washing of the needles, wherein the washing-facing position includes an internal washing-facing position at which the needles face the internal washing hole and an external washing-facing position at which the needles face the external washing hole, and wherein the act of washing the needles includes:
  positioning the needles at the internal washing-facing position;
  advancing the needles from the internal washing-facing position and internally washing the needles in the internal washing hole;
  positioning the needles at the internal washing-facing position by retracting the needles from the internal washing hole;
  positioning the needles at the external washing-facing position by rotating the needles from the internal washing-facing position; and
  advancing the needles from the external washing-facing position and externally washing the needles in the external washing hole.

13. The method of claim 8, further comprising:
positioning the needles at the washing-facing position by retracting the needles from the washer;
positioning the needles at a bypass-facing position at which the needles face a bypass part for bringing the needles into communication with each other, by rotating the needles from the washing-facing position; and
advancing the needles from the bypass-facing position and bringing the needles into communication with each other in the bypass part.

14. The method of claim 8, further comprising:
positioning the needles at the washing-facing position by retracting the needles from the washer;
positioning the needles at a sterilization-facing position at which the needles face a sterilizer for sterilizing the needles, by rotating the needles from the washing-facing position; and
advancing the needles from the sterilization-facing position and sterilizing the needles in the sterilizer.

15. The method of claim 14, further comprising:
positioning the needles at the sterilization-facing position by retracting the needles from the sterilizer;
positioning the needles at a bypass-facing position at which the needles face a bypass part for bringing the needles into communication with each other, by rotating the needles from the sterilization-facing position; and
advancing the needles from the bypass-facing position and bringing the needles into communication with each other in the bypass part.

* * * * *